United States Patent
Wiklander et al.

(10) Patent No.: US 11,298,319 B2
(45) Date of Patent: Apr. 12, 2022

(54) CELL PENETRATING PEPTIDE (CPP)-MEDIATED EV LOADING

(71) Applicant: Evox Therapeutics Ltd, Oxford (GB)

(72) Inventors: Oscar Wiklander, Solna (SE); Per Lundin, Stockholm (SE); Dhanu Gupta, Stockholm (SE)

(73) Assignee: Evox Therapeutics Ltd, Oxford (GB)

( * ) Notice: Subject to any disclaimer, the term of this patent is extended or adjusted under 35 U.S.C. 154(b) by 490 days.

(21) Appl. No.: 16/317,455

(22) PCT Filed: Jul. 10, 2017

(86) PCT No.: PCT/EP2017/067297
§ 371 (c)(1),
(2) Date: Jan. 11, 2019

(87) PCT Pub. No.: WO2018/011153
PCT Pub. Date: Jan. 18, 2018

(65) Prior Publication Data
US 2019/0388347 A1    Dec. 26, 2019

(30) Foreign Application Priority Data

Jul. 11, 2016 (GB) ...................................... 1611988

(51) Int. Cl.
*A61K 47/69* (2017.01)
*A61K 9/127* (2006.01)
(Continued)

(52) U.S. Cl.
CPC .......... *A61K 9/1271* (2013.01); *A61K 9/5068* (2013.01); *A61K 47/54* (2017.08); *A61K 47/61* (2017.08); *A61K 47/645* (2017.08); *A61K 47/6901* (2017.08); *A61K 47/6911* (2017.08); *A61K 47/6951* (2017.08); *A61K 47/6957* (2017.08); *C12N 15/88* (2013.01)

(58) Field of Classification Search
CPC ................................................... A61K 47/6911
See application file for complete search history.

(56) References Cited

U.S. PATENT DOCUMENTS

2010/0047334 A1    2/2010  Stavroula
2012/0022002 A1*   1/2012  Rivers ................ A61K 47/6455
                                                                    514/20.8

FOREIGN PATENT DOCUMENTS

WO    WO 2001/0203 31 A1    3/2001
WO    WO 2013/084000 A2     6/2013
(Continued)

OTHER PUBLICATIONS

He et al (Journal of Controlled Release 176 (2014) 123-132). (Year: 2014).*

(Continued)

*Primary Examiner* — Benjamin J Packard
(74) *Attorney, Agent, or Firm* — Cooley LLP; Matthew Pavao; (Chris) Chun L. Yu

(57) ABSTRACT

The present invention relates to methods for loading extracellular vesicles (EVs) with a pharmacological agent. The invention discloses the use of cell-penetrating peptides as carriers into EVs, using either a non-covalent or covalent loading approach. Furthermore, the present invention pertains to medical uses and compositions comprising such pharmacological agent-loaded EVs.

6 Claims, 7 Drawing Sheets

Specification includes a Sequence Listing.

(51) Int. Cl.
  *A61K 47/61* (2017.01)
  *A61K 47/64* (2017.01)
  *A61K 47/54* (2017.01)
  *A61K 9/50* (2006.01)
  *C12N 15/88* (2006.01)

(56) References Cited

FOREIGN PATENT DOCUMENTS

| WO | WO 2014/168548 A2 | 10/2014 |
| WO | WO 2015/120150 A1 | 8/2015 |
| WO | WO 2016/033695 A1 | 3/2016 |
| WO | WO 2016/044947 A1 | 3/2016 |

OTHER PUBLICATIONS

El-Andaloussi (Nature Protocols, vol. 7 No. 12 (2012) 2112-2126). (Year: 2012).*
Lin et al. "Thermosensitive magnetic liposomes with doxorubicin cell-penetrating peptides conjugate for enhanced and targeted cancer therapy", Drug Delivery, vol. 23, No. 9, 2016, p. 3436-3443.
Yang Y. et al. "PEGylated liposomes with NGR ligand and heat-activable cell-penetrating peptide-doxorubicin conjugate for tumor-specific therapy", Biomaterials, vol. 35, Issue 14, 2014,p. 4368-4381.

\* cited by examiner

SEQUENCE LISTING

<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: Rationally-designed to act as a
      Cell-Penetrating Peptide (CPP)

<400> SEQUENCE: 1

Gly Leu Trp Trp Lys Ala Trp Trp Lys Ala Trp Trp Lys Ser Leu Trp
1               5                   10                  15

Trp Arg Lys Arg Lys Arg Lys Ala
            20

CELL PENETRATING PEPTIDE (CPP)-MEDIATED EV LOADING

RELATED APPLICATIONS

This application is a U.S. National Phase Application, filed under 35 U.S.C. § 371, of International PCT Application No. PCT/EP2017/067297, filed Jul. 10, 2017, which claims the priority benefit of GB 1611988.5, filed Jul. 11, 2016, the contents of each of which are herein incorporated by reference in their entirety.

INCORPORATION-BY-REFERENCE OF SEQUENCE LISTING

The contents of the file named "EVOX-004_N01US SeqListing_ST25", which was created on Aug. 26, 2019, and is 0.66 MB in size are hereby incorporated by reference in their entirety

TECHNICAL FIELD

The present invention relates to methods for loading extracellular vesicles (EVs) with pharmacological agents and uses of such EVs for therapeutic purposes.

BACKGROUND ART

Extracellular vesicles (EVs) modulate cell-to-cell communication in normal physiology and pathology by presenting their contents (primarily RNAs, proteins, and lipids) to recipient cells in target tissues. Modification of EVs to incorporate various types of pharmacological agents have been explored in numerous contexts, for instance WO2013/084000, which discloses the use of exosomes for intracellular delivery of biotherapeutics, or WO2010/119256, which describes delivery of exogenous genetic material using exosomes.

The utility of EVs as drug delivery vehicles is unquestionable in the case of for instance nucleic acid based drugs such as siRNA, large protein-based drugs targeting intracellular components, and e.g. poorly soluble or highly toxic pharmacological agents. EV-mediated pharmacological agent delivery for a broader set of pharmacological agents has also been explored to some extent, with for instance WO2011/097480 representing the typical approach to loading of EVs with organic small molecule compounds. WO2011/097480 describes a very facile method wherein e.g. the phytochemical agents curcumin and resveratrol are loaded into EVs using a simple co-incubation step during which purified EVs and free drug (e.g. curcumin) are allowed to incubate together in phosphate buffered saline (PBS) at room temperature, relying on diffusion of the drug into the EV. Although highly convenient and straightforward, this conventional approach to loading simple pharmacological agents into EVs is not particularly efficient, results in significant waste of the pharmacological agent, and is also very difficult to control. Also, it suffers from lack of general applicability, as some pharmacological agents will not load into EVs in high quantities only using co-incubation. Others (for instance Fuhrman et al, J. Control Rel., 2015) have also evaluated permeabilization of EVs, using detergents such as saponin, as a way of increasing the loading efficiency of in this case the photoactive agent porphyrin. A recent patent application (WO2015/120150) is also concerned with loading of tumor-derived EVs with various types of anticancer drugs, covering both small molecular agents and large biopharmaceuticals. However, as is often the case in the art, very little information is available on how to load exosomes and if there are methods available they are rarely useful for loading and actual therapeutic application of pharmacological agent-carrying EVs.

SUMMARY OF THE INVENTION

It is hence an object of the present invention to overcome the above-identified problems associated with the loading of pharmacological agents into EVs for subsequent therapeutic, prophylactic and/or diagnostic application. Furthermore, the present invention aims to satisfy other existing needs within the art, for instance to enable loading of significant amounts of pharmacological agents into EVs, to enable controllable loading, and to provide pharmacological agent-loaded EVs with considerable therapeutic potential. Furthermore, the present invention provides for a generally applicable strategy for loading of pharmacological agents of various origins (small organic compounds, RNA therapeutics, peptides and proteins, etc.) into EVs, which has been lacking in the art.

The present invention achieves these and other objectives by utilizing cell-penetrating peptides (CPPs) as a carrier of pharmacological agents into EVs. In one aspect, the present invention relates to methods for EV loading comprising the step of exposing a population of EVs to at least one pharmacological agent and at least one CPP. The pharmacological agent and the CPP may be covalently conjugated into a single conjugate, with one CPP carrying at least one pharmacological agent. Alternatively, the CPP and pharmacological agent may also form nanoparticle complexes as a result of non-covalent interactions, which may be surmised to be e.g. hydrophobic and/or electrostatic and/or van der Waals interactions. Interestingly, although CPP-pharmacological agent conjugates may be present in the form of individual conjugates they may also form non-covalent nanoparticle complexes. The term pharmacological agent as used herein encompasses, as above-mentioned, a wide variety of different types of molecules, including peptides, nucleic acid-based agents such as siRNA or mRNA, and organic pharmacological agents.

In a further aspect, the present invention pertains to methods of loading EVs with pharmacological agents through loading of the EV source cells. Such methods may comprise the steps of (a) exposing a population of EV source cells to at least one pharmacological agent and at least one CPP and (b) harvesting EVs produced by the EV source cells, wherein the EVs comprise pharmacological agent(s) in question.

The loading methods as per the present invention may in certain instances advantageously be combined with an electroporation step, in order to increase the quantity of drug loaded into the EVs.

In another aspect, the present invention pertains to EVs comprising at least one pharmacological agent conjugated to or complexed with at least one CPP, and also to EVs within which pharmacological agents has been released from a CPP conjugate and/or a CPP nanoparticle complex. The pharmacological agents of the present invention may be selected from a wide variety of drug or diagnostic agent categories, for instance anticancer agents such as doxorubicin, 5-fluorouracil or other nucleoside analogues such as cytosine arabinoside, proteasome inhibitors such as bortezomib, or kinase inhibitors such as imatinib or seliciclib, or NSAIDs such as naproxen, aspirin, or celecoxib, antibiotics such as heracillin, antihypertensives such as ACE inhibitors such as enalapril, short interfering RNAs for silencing of various target genes, mRNA and modified mRNAs to enable delivery of a protein-coding agent, splice-switching RNAs to change splicing patterns, peptides with pharmacological activity or endosomal escape activity, protein therapeutics, etc.

In yet another aspect, the present invention pertains to methods for delivering pharmacological agents to a target cell, a target tissue, a target organ, or to any target compartment (which may also include bodily fluids, for instance the blood stream or cerebrospinal fluid). Such methods may comprise exposing the target to EV loaded with a pharmacological agent using the CPP-mediated strategies of the present invention.

In a further aspect, the present invention also provides methods of altering the pharmacokinetic or pharmacodynamics profile of a pharmacological agent. Such methods involve CPP-mediated loading of the pharmacological agent in question into an EV, in order to modulate in vivo and potentially also in vitro properties of the pharmacological agent in question.

Additionally, in further aspects, the present invention pertains to pharmaceutical compositions comprising pharmacological agent-carrying EVs as per the present invention, or in practical terms compositions comprising populations of pharmacological agent-carrying EVs as per the present invention. The EV concentration in such compositions may be expressed in many different ways, for instance amount of EV protein per unit (often volume) or per dose, number of particles (i.e. EVs) per unit (often volume or per unit of body weight) or per dose, concentration of pharmacological agent per unit or per dose, etc. Typically, such pharmaceutical compositions are formulated for in use in vivo and also in vitro using pharmaceutically acceptable excipients.

Finally, the present invention also relates to medical uses and applications of pharmacological agent-carrying EVs, for instance in the treatment of inflammatory diseases, autoimmune diseases, cancer, lysosomal storage disorders, orphan diseases, metabolic disorders, or any suitable disease or disorder that could be treated using the EVs per the present invention.

DETAILED DESCRIPTION OF THE INVENTION

Figure 1:
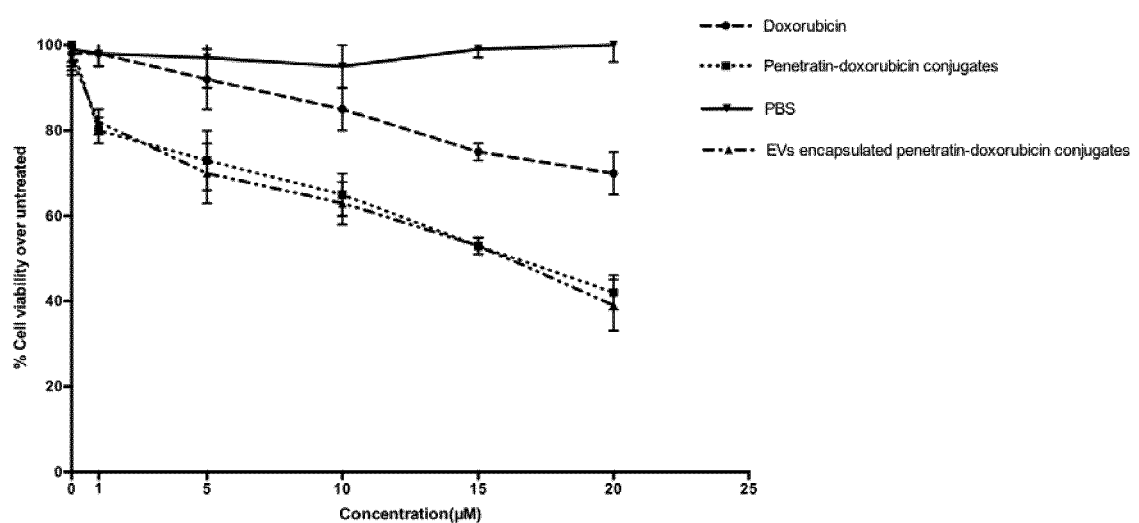
FIG. 1 shows the effect of immune cell-derived EVs loaded with CPP-doxurubicin conjugates on proliferation of MDA-MB-231 cells. MTT assay showing the cytotoxicity of the MDA-MB-231-R upon treatment with free doxorubicin, EVs loaded with penetratin-doxorubicin conjugates, and free penetrating-doxorubicin conjugates. Cells were treated with different doses (1 μM, 5 μM, 10 μM, 15 μM and 20 μM) and after 24 hours of treatment doxorubicin-mediated cytotoxicity between the cells was determined by MTT assay.

The present invention describes inter alia novel methods, compositions, and uses of EVs for the delivery of pharmacological agents. More specifically, the present invention relates to methods for EV loading, EVs loaded with pharmacological agents, various methods for utilizing such EVs, pharmaceutical compositions comprising EVs in therapeutically effective amounts, and medical uses of pharmacological agent-loaded EVs as per the present invention.

For convenience and clarity, certain terms employed herein are collected and described below. Unless otherwise defined, all technical and scientific terms used herein have the same meaning as commonly understood by one of ordinary skill in the art to which this invention belongs.

Where features, aspects, embodiments, or alternatives of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the various pharmacological agents described in connection with the methods for CPP-mediated loading of EVs are to be understood to be disclosed, relevant and included also in the context of the pharmaceutical compositions comprising pharmacological agent-carrying EVs. Furthermore, certain embodiments described in connection with certain aspects, for instance the administration routes of the pharmacological agent-loaded EVs, as described in relation to aspects pertaining to treating certain medical indications with EVs as such, may naturally also be relevant in connection with other aspects and/or embodiment such as those pertaining to the pharmaceutical compositions of the present invention. Moreover, any and all features (for instance any and all members of a Markush group) can be freely combined with any and all other features (for instance any and all members of any other Markush group), e.g. any EV protein may be combined with any targeting moiety, or any EV cell source may be combined with any pharmacological agent. Furthermore, when teachings herein refer to EVs in singular and/or to EVs as discrete natural nanoparticle-like vesicles it should be understood that all such teachings are equally relevant for and applicable to a plurality of EVs and populations of EVs. As a general remark, the pharmacological agents, the CPPs, the targeting moieties, the parental cell sources, the exosomal proteins, and all other aspects, embodiments, and alternatives in accordance with the present invention may be freely combined in any and all possible combinations without deviating from the scope and the gist of the invention. Furthermore, any polypeptide or polynucleotide or any polypeptide or polynucleotide sequences (amino acid sequences or nucleotide sequences, respectively) of the present invention may deviate considerably from the original polypeptides, polynucleotides and sequences as long as any given molecule retains the ability to carry out the technical effect associated therewith. As long as their biological properties are retained the polypeptide and/or polynucleotide sequences according to the present application may deviate with as much as 50% (calculated using for instance BLAST or ClustalW) as compared to the native sequence, although a sequence identity that is as high as possible is preferable (for instance 60%, 70%, 80%, or e.g. 90% or higher). The combination (fusion) of e.g. at least one targeting polypeptide and at least one EV protein or e.g. at least one CPP and at least one pharmacological agent in the form of a peptide implies that certain segments of the respective polypeptides may be replaced and/or modified, meaning that the deviation from the native sequence may be considerable as long as the key properties (e.g. targeting properties, trafficking to the surface of exosomes, therapeutic activity, potency, etc.) are maintained. Similar reasoning thus naturally applies to the polynucleotide sequences encoding for such polypeptides.

The terms "extracellular vesicle" or "EV" or "exosome" are used interchangeably herein and shall be understood to relate to any type of vesicle that is obtainable from a cell in any form, for instance a microvesicle (e.g. any vesicle shed from the plasma membrane of a cell), an exosome (e.g. any vesicle derived from the endo-lysosomal pathway), an apoptotic body (e.g. obtainable from apoptotic cells), a microparticle (which may be derived from e.g. platelets), an ectosome (derivable from e.g. neutrophils and monocytes in serum), prostatosome (e.g. obtainable from prostate cancer cells), or a cardiosome (e.g. derivable from cardiac cells), etc. Furthermore, the said terms shall also be understood to relate to extracellular vesicle mimics, cell and/or cell membrane-based vesicles obtained through cell extrusion, membrane extrusion, vesicle extrusion, or other techniques, etc. Essentially, the present invention may relate to any type of lipid-based structure (with vesicular morphology or with any other type of suitable morphology) that can act as a delivery or transport vehicle for pharmacological agents of interest. It will be clear to the skilled artisan that when describing medical and scientific uses and applications of the EVs, the present invention normally relates to a plurality of EVs, i.e. a population of EVs which may comprise thousands, millions, billions or even trillions of EVs. As can be seen from the experimental section below, EVs may be present in concentrations such as $10^5$, $10^8$, $10^{11}$, $10^{15}$, $10^{18}$, $10^{25}$, $10^{30}$ EVs (often termed "particles") per unit of volume (for instance per ml), or any other number larger, smaller or anywhere in between. In the same vein, the term "population", which may e.g. relate to an EV comprising a certain pharmacological agent and often a certain CPP, shall be understood to encompass a plurality of entities constituting such a population. In other words, individual EVs when present in a plurality constitute an EV population. Thus, naturally, the present invention pertains both to individual EVs comprising pharmacological agents and populations comprising EVs comprising pharmacological agents, as will be clear to the skilled person. The dosages of EVs when applied in vivo may naturally vary considerably depending on the disease to be treated, the administration route, the pharmacological agent cargo, etc.

The term "pharmacological agent" or "pharmacologically active agent" or "therapeutic agent" or "drug" or "pharmacological drug" or "pharmacological therapeutic" are used interchangeably herein and shall be understood to relate to any molecular agent which may be used for the treatment and/or diagnosis of a disease and/or disorder. Pharmacological agents as per the present invention encompass a wide variety of pharmacologically or pharmaceutically active agents, including (i) organic compounds with pharmacological activity which are normally synthesized via chemical synthesis, (ii) naturally derived compounds which may for instance be obtained via purification from natural sources, (iii) nucleic acid-based compounds of various kinds, for instance oligonucleotides such as siRNA, splice-switching RNA, CRISPR guide strands, short hairpin RNA (shRNA), antisense oligonucleotides, polynucleotides such as mRNA, and in particular nucleic acid-based agents which are chemically synthesized and/or which comprise chemically modified nucleotides such as 2'-O-Me, 2'-O-Allyl, 2'-O-MOE, 2'-F, 2'-CE, 2'-EA 2'-FANA, LNA, CLNA, ENA, PNA, phosphorothioates, tricyclo-DNA, etc., (iii) peptides and polypeptides (i.e. proteins) of any kind, for instance obtained via peptides synthesis or via recombinant protein production, and (iv) essentially any type of pharmacological and/or pharmaceutically active agent which can be made to interact with CPPs. The present invention is naturally applicable also to other pharmacological agents without departing from the gist of the invention, as would be clear to a person skilled in the art.

The terms "cell-penetrating peptide" and "CPP" are used interchangeably herein and shall be understood to relate to relatively short peptides (typically less than 50 amino acids but the CPPs as per the present invention may also be longer) with the ability to gain access to the interior of virtually any cell type. CPPs are typically highly cationic and rich in arginine and/or lysine amino acids. Many effective CPPs are furthermore amphipathic, having stretches of hydrophobic amino acids. Additionally, some CPPs may have aliphatic spacers interspersed between the amino acids, in order to modulate hydrophobicity, binding properties, amphipathicity, etc. As is shown herein, CPPs have the exceptional property of being able to carry into cells and/or EVs a wide variety of covalently (conjugated) and/or non-covalently attached cargoes such as proteins, oligonucleotides, organic compounds, and as in the present invention pharmacological agent. CPPs as per the present invention includes, but are not limited to, transportan, transportan 10, penetratin, MTS, VP22, CADY peptides, MAP, KALA, PpTG20, proline-rich peptides, MPG peptides, PepFect peptides, Pep-1, L-oligomers, calcitonin-peptides, arginine-rich CPPs such as poly-Arg, Tat, and combinations thereof. CPPs in accordance with the present invention also includes similar classes of peptides such as antimicrobial peptides, membrane-active peptides, and peptidic ligands to receptors that are already present on EV membrane which may facilitate internalization or interaction with an EV. Furthermore, various types of chemical modifications have been introduced on CPPs with great success, and the CPPs of the present invention may thus be modified through the introduction of for instance lipid tails, cholesterol and cholesterol analogues, quinolones and specifically chloroquine and its fluorinated analogues, polyhistidine and other types of C- and/or N-terminal and/or orthogonal modifications. These types of chemical modifications may for example improve complexation of pharmacological agents, internalization into EVs or interaction with the EV surface, in addition to modulating size and zeta potential. In addition to chemical modifications being made to CPPs per se, the CPPs per the present invention may include synthetic and/or artificial peptide derivatives, for instance so called peptidoids which includes CPPs containing non-natural amino acids, inverso and/or retro-inverso analogues, modifications from L- to D-amino acids, linear or branched aliphatic chains, peptides containing residues that mimic protein post-translational modifications, and other types of desirable modifications known to the person skilled in the art. Furthermore, as is clear in the context of CPP-pharmacological agent conjugates, CPPs may be functionalized to comprise moieties that enable chemical conjugation or even complexation with the pharmacological agent cargo.

The terms "EV protein", "exosomal protein", "exosomal sorting domain", "EV sorting domain", "EV sorting protein", "exosomal protein", "exosomal polypeptide", "EV polypeptide", etc. are used interchangeably herein and shall be understood to relate to any polypeptide that can be utilized to transport a polypeptide construct (which typically comprises, in addition to the EV protein, at least one protein of interest) to a suitable vesicular structure, i.e. to a suitable EV. More specifically, said terms shall be understood as comprising any polypeptide that enables transporting, trafficking or shuttling of a polypeptide construct to a vesicular structure, such as an exosome. Examples of such exosomal sorting domains are for instance CD9, CD53, CD63, CD81, CD54, CD50, FLOT1, FLOT2, CD49d, CD71, CD133, CD138, CD235a, ALIX, Syntenin-1, Syntenin-2, Lamp2b, TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11 b, CD11c, CD18/ITGB2, CD41, CD49b, CD49c, CD49e, CD51, CD61, CD104, Fc receptors, interleukin receptors, immunoglobulins, MHC-I or MHC-II components, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, VTI1B, and any combinations thereof, but numerous other polypeptides capable of transporting a polypeptide construct to an EV are comprised within the scope of the present invention. The EV proteins as per the present invention are typically of human origin and can be found in various publicly available databases such as Uniprot, RCSB, etc. The EV proteins may be fused to various other proteins and/or protein domains, to for instance enhance the surface display, increase avidity, or enable interaction with particular types of binding proteins in a non-covalent manner.

The terms "source cell" or "EV source cell" or "parental cell" or "cell source" or "EV-producing cell" or any other similar terminology shall be understood to relate to any type of cell that is capable of producing EVs under suitable conditions, for instance in suspension culture or in adherent culture or any in other type of culturing system. Source cells as per the present invention may also include cells producing exosomes in vivo. The source cells per the present invention may be select from a wide range of cells and cell lines, for instance mesenchymal stem or stromal cells or fibroblasts (obtainable from e.g. bone marrow, adipose tissue, Wharton's jelly, perinatal tissue, tooth buds, umbilical cord blood, skin tissue, etc.), amnion cells and more specifically amnion epithelial cells optionally expressing various early markers, myeloid suppressor cells, M2 polarized macrophages, adipocytes, endothelial cells, fibroblasts, etc. Cell lines of particular interest include human umbilical cord endothelial cells (HUVECs), human embryonic kidney (HEK) cells, endothelial cell lines such as microvascular or lymphatic endothelial cells, chondrocytes, MSCs of different origin, airway or alveolar epithelial cells, fibroblasts, endothelial cells, etc. Also, immune cells such as B cells, T cells, NK cells, macrophages, monocytes, dendritic cells (DCs) are also within the scope of the present invention, and essentially any type of cell which is capable of producing EVs is also encompassed herein.

In a first aspect, the present invention relates to methods for loading EVs with pharmacological agents, wherein the methods comprise exposing a population of EVs to at least one pharmacological agent and at least one CPP. CPPs, which normally comprise a mix of cationic and hydrophobic amino acid residues, are either covalently conjugated to or non-covalently complexed with the pharmacological agent cargo. Non-covalent complexes between CPPs and the pharmacological agent normally form nanoparticle-like structures which can be studied and characterized with conventional techniques for nanoparticle research, for instance dynamic light scattering and nanoparticle tracking analysis. Conjugates between pharmacological agents and CPPs occasionally also form nanoparticles, due to e.g. electrostatic and/or hydrophobic interactions between individual conjugates leading to aggregation into supramolecular structures. Regardless of the whether the complexes comprise non-covalent or conjugated pharmacological agents and CPPs such complexes may display certain nanoparticle-like features, such as size and zeta potential. The zeta potential of the complexes of present invention may vary substantially depending on the CPP and the pharmacological agent in question, but advantageously the zeta potential is either positive or negative with an absolute value of preferably +/−10 mV, more preferably +/−20 mV, or even more preferably +/−30 mV, or even higher/lower, in order to display colloidal stability. The sizes of such nanoparticle complexes may also vary considerably but in order to enable efficient incorporation into EVs it is preferably if the size of the complex is smaller than the size of the EV. As an example, an EV of a size of 120 nm would preferably be loaded with a pharmacological agent in the form of a CPP-containing nanoparticle having a size well below 120 nm, e.g. 10 nm.

In a further aspect, the present invention pertains to methods of loading EVs with pharmacological agents through loading of the EV source cells. This approach is especially advantageous when using CPPs or virally derived peptides that are known to internalize into cellular compartments associated with production/secretion of EVs, for instance the endo-lysosomal pathways and the plasma membrane. Such methods may comprise the steps of (a) exposing a population of EV source cells to at least one pharmacological agent and at least one CPP and (b) harvesting EVs produced by the EV source cells, wherein the EVs comprise the pharmacological agent(s) in question.

As above-mentioned, in certain aspects of the invention the at least one pharmacological agent and the at least one CPP may be present in the form or covalent conjugates, non-covalent complexes or a combination thereof. There are multiple strategies available for covalent conjugation/linkage, for instance the formation between a CPP and a pharmacological agent of any type of chemical bond selected for instance from the group comprising an ester bond, an amide bond, a disulfide bond, a thioether bond, a biotin-streptavidin interaction, a linkage obtained through a maleimide-NHS reaction, a linkage obtained through a EDC-NHS reaction, a stapled linkage (for instance an all-hydrocarbon staple) and various other conjugation techniques.

In yet another embodiment, the loading of the CPP-pharmacological agent complexes and/or conjugates may be enhanced through the use of a transfection reagent, such as a liposome and/or a lipid nanoparticle. By combining CPPs and a transfection reagent one can in certain instances improve the pharmacological agent loading into EVs and into the EV source cells if that method is utilized. Furthermore, the use of electroporation can also increase the loading into the EVs, and electroporation can also be employed together with the use of transfection reagents. Electroporation may be carried out using voltages in the range of 20V/cm to 1000V/cm, often 20V/cm to 100V/cm. The capacitance of the electroporation step is normally between 25 µF and 250 µF, such as between 25 µF and 125 µF, although these parameters may vary extensively depending on various factors such as the EV source cells, any genetic or chemical modification of the EV, the nature of the CPP, the nature of the pharmacological agent, etc.

In yet another aspect, the present invention relates to an EV comprising at least one pharmacological agent conjugated to and/or complexed with at least one CPP. Furthermore, the present invention also pertains to EVs within which the at least one pharmacological agent has been released from the at least one CPP conjugate and/or CPP complex inside the EV. The terms "inside the EV" and "in the EV" shall be understood to comprise the EV in its entirety, including the membrane of the EV, or even onto the external surface of the EV, as long as the pharmacological agent is in some way interacting with the EV and wherein the EVs are carrying, in any way, pharmacological agent(s) per se.

As abovementioned, the pharmacological agents as per the present invention can be obtained from essentially the entire space of pharmaceutically and/or pharmacologically and/or diagnostically relevant agents, for instance anticancer agents, cytostatic agents, tyrosine kinase inhibitors, statins, NSAIDs, antibiotics, antifungal agents, antibacterial agents, anti-inflammatory agents, anti-fibrotics, antihypertensives, aromatase or esterase inhibitors, an anticholinergics, SSRIs, BKT inhibitors, PPAR agonists, HER inhibitors, AKT inhibitors, BCR-ABL inhibitors, signal transduction inhibitors, angiogenesis inhibitors, synthase inhibitors, ALK inhibitors, BRAF inhibitors, MEK inhibitors, PI3K inhibitors, neprilysin inhibitors, beta2-agonists, CRTH2 antagonists, FXR agonists, BACE inhibitors, sphingosine-1-phosphate receptor modulators, MAPK inhibitors, Hedgehog signaling inhibitors, MDM2 antagonists, LSD1 inhibitors, lactamase inhibitors, TLR agonists, TLR antagonists, IDO inhibitors, ERK inhibitors, Chk1 inhibitors, splicing modulatory, DNA or RNA intercalators, etc. Other non-limiting examples of pharmacological agents as per the present invention includes for instance everolimus, trabectedin, abraxane, pazopanib, enzastaurin, vandetanib, a FLT-3 inhibitor, a VEGFR inhibitor, an EGFR TK inhibitor, an aurora kinase inhibitor, a PIK-1 modulator, a Bcl-2 inhibitor, an HDAC inhbitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, pemetrexed, erlotinib, dasatanib, nilotinib, decatanib, panitumumab, amrubicin, oregovomab, nolatrexed, batabulin, ofatumumab, zanolimumab, edotecarin, tetrandrine, rubitecan, tesmilifene, oblimersen, ticilimumab, ipilimumab, gossypol, cilengitide, gimatecan, lucanthone, neuradiab, vitespan, talampanel, atrasentan, romidepsin, sunitinib, 5-fluorouracil, vorinostat, etoposide, gemcitabine, doxorubicin, 5'-deoxy-5-fluorouridine, vincristine, temozolomide, seliciclib, capecitabine, camptothecin, PEG-labeled irinotecan, tamoxifen, toremifene citrate, anastrazole, exemestane, letrozole, vatalanib, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, erlotinib, lapatanib, canertinib, lonafarnib, tipifarnib, amifostine, suberoyl analide hydroxamic acid, valproic acid, trichostatin sorafenib, arnsacrine, anagrelide, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, squalamine, endostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, droloxifene, 4-hydroxytamoxifen, pipendoxifene, arzoxifene, fulvestrant, acolbifene, lasofoxifene, idoxifene, topotecan, rapamycin, temsirolimus, zolendronate, prednisone, lenalidomide, gemtuzumab, hydrocortisone, dexrazoxane, alemtuzumab, all-transretinoic acid, ketoconazole, megestrol, immune globulin, nitrogen mustard,methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, efavirinz among others. Furthermore, as abovementioned, the pharmacological agents as per the present invention also includes naturally derived compounds which may for instance be obtained via purification from natural sources, any type of nucleic acid-based compounds, for instance oligonucleotides such as siRNA, splice-switching RNA, CRISPR guide strands, short hairpin RNA, antisense oligonucleotides, mRNA, and in particular nucleic acid-based agents which are chemically synthesized and/or which comprise chemically modified nucleotides such as 2'-O-Me, 2'-O-Allyl, 2'-O-MOE, 2'-F, 2'-CE, 2'-EA 2'-FANA, LNA, CLNA, ENA, PNA, phosphorothioates, tricyclo-DNA, etc. Furthermore, peptides and polypeptides, and not only peptides and/or proteins obtainable via peptide synthesis but also peptides and proteins obtainable through recombinant protein production, are also comprised within the definition of the pharmacological agents as per the present invention. As mentioned above, the present invention is naturally applicable also to other pharmacological agents without departing from the gist of the invention, as would be clear to a person skilled in the art.

In a further embodiment, the CPPs for loading of pharmacological agents into EVs and/or EV source cells may be selected from a large variety of CPPs including, but not limited to: transportan, transportan 10, penetratin, CADY peptides such as CADY-1, MTS, VP22, MAP, KALA, PpTG20, prolin-rich peptides, MPG peptides, PepFect peptides, Pep-1, L-oligomers, calcitonin-peptides, arginine-rich CPPs such as poly-Arg, Tat, (1-9)-(38-42)Crot, (1-9)-Ahx-(38-42)Crot, (42-38)-(9-1)Crot, (KFF)3K, (KH)9-Bp100, (RW)4, 435Bpeptide, 439Apeptide, 7Arg, A, A1, A10, A11, A12, A2, A3, A4, A5, A6, A7, A8, A9, ABL-1, Ac-Penetratin-substrate, Ac-pep5-cpp, Ac-TAT-substrate, AcD11, AcD4, AcD6, AcD7, acFTAT, ACPP, AgNP-TAT, ALPHA-Virusnucleocapsid(311-320), AlphaVirusP130(227-234), APP521, ARF(1-22), ARF(1-37), ARF(19-31), ARF(2-14), Arg5-ELPBC, Arg8-ELPBC, Arg9, ArgdeletionmutantofTat (48-60), Asn-Oct-6, B, b-WT1-pTj, B1, B1-Leu, B1-Lys, B5, B6, B8, B9, BagP, betaZipTF, BF2d, Bip1, Bip10, Bip11, Bip12, Bip13, Bip14, Bip15, Bip16, Bip17, Bip18, Bip19, Bip2, Bip3, Bip4, Bip5, Bip6, Bip7, Bip8, Bip9, BipartitenucleoplasminNLS(155-170), BMVGAG, BMVGag(7-25), BovinePrp(1-30), BP326, BP328, BP330, Buforin-II, C, c-Myc-R11, C.eSDC3, C1, C1-pep5-cpp, C105Y, C105Yderivative, C11, C16NTD, C2, C2-pep5-cpp, C24-LMWP, C3, C4, C4-pep5-cpp, C45D18, C5, C5-pep5-cpp, C6, C6-pep5-cpp, C7-pep5-cpp, CA3, CA4, CA5, CA6, CA6L, CAD-2(des-acetyl, Lysl 9-CADY), CADY-1, CADY2, cAMPdependentTF, Camptide, CAR, CCMVGAG, CendRP, CF-BP16, CF-Penetratin-substrate, CF-sC18, CF-TAT-substrate, CF-Tat.48-60, CH2R4H2C, CL22, CPPecp, CPPK, CPPL, CPPP-2, cRGD, CRGDK, Crot(27-39), Crotamine, CS-Lin-Pen, CSK, CTP, CTP50, CTP501, CTP502, CTP503, CTP504, CTP505, CTP506, CTP507, CTP508, CTP509, CTP510, CTP511, CTP512, CTP513, CTP514x, cyclic[W(RW)4], CyclinLania-6a, CyLoP-1, Cys(BSH)-Arg11-NH2, Cys(BSH)-Lys[Cys(BSH)-]Arg11-NH2, Cys(BSH)-R11, Cys(BSH)-TAT, Cyt4-13, Cyt5-13, Cyt79-88, Cyt79-92, Cytc-ss-MAP, Cytc-ss-R8, Cytc(5-13), CytC71-101, CytC86-101, d-NTD, D-TAT, D1, D10, D11, D12, D2, D3, D4, D5, D6, D7, D8, D9, DerivativeofKLA1, DermaseptinS4, Dformof(1-9)-(38-42)Crot, dfTAT, DNA-IL-PEI, Dox-pVEC-gHo(Dox-gHoPe2), DOX-T7-TAT-LIP, DOX-TAT-LIP, DPV10, DPV10/6, DPV1047, DPV1048, DPV15, DPV15b, DPV3, DPV3/10, DPV6, DPV7, DPV7b, DS4.3, DSPE-PEG-2K-TAT, DSPE-PEG-CPP(CPP-Lp), EB-1, EB1, EB1-Cys, ECP(32-38), ECP(32-39), ECP(32-40), ECP(32-41), ECP(32-41)R3Q, ECP(32-41)W4R, ECP(33-40), ECP(33-41), ECP(34-41), EDN(32-41), EF, Engrailed(454-513), Ernst Erns10, Erns11, Erns2, Erns3, Erns4, Erns5, Erns6, Erns7, Erns8, Erns9, F(SG)4Pen, F(SG)4R8, F(SG)4TP10, F10, F3, F3Peptide, F4, F4R8-PAD, F7, F8, FabRev1-Tat, fGeT, FHV-TA(39-49), FHV(40-49), FHVcoat(35-49), FHVgammapeptide, FHVPeptide, Foxp3-11R, FP-lipo, fTAT, G(SG)4Pen, G(SG)4R8, G(SG)4TP10, G3R6TAT, G53-4, G55-9, GALA, Galanin, GC/R8-Lip, GCN-4, Gd3+-DOTA-CAT, GKKpeptide, Glu, Glu-Ala, Glu-Lys, Glu-Oct-6, GV1001, H16R8, H8R15, HATF3, HB-EGF, hBCPP, hClock-(35-47), HEI, HEN1/NSLC1, HEN2/NSLC2, HEO, Herpesvirus8k8protein(124-135), HipC, HIV-1Rev(34-50), HIV-1Tat(48-60), HIV-1TATpeptide-Crystall ins, HIV-TAT, HIV-TAT(47-57), hLF(38-59)peptide, hLF+4R, hLFK7, hLFlin+4R, hLFM9A, hLFP15A, hLFpeptide, hLFQ6A, hLFR13A, hLFR13A/P15R, hLFR7, hLFR7A, hLFR7A/V12R, hLFV12R, hLFW5A, hLFWT, HME-1, HN-1, HNF3, hPER1-PTD, hPER1-PTD(830-846)NLS, hPER3NLS, Hph-1, HR9, HTLV-IIRex(4-16), HumancFos (139-164), HumancJun(252-279), HumanPrp(1-28), HumanU2AF(142-153), I, I-TYR-L-Mca, IA0(Bicyclic)(integralargininepeptides), IA2, IA4a, IA4b, IA52H1W, IA6a, IA6b, IA6c, IA6d, IA8a, IA8b, IA8bL(Linearvariants), II, III, IL-13p, iNGR, Inv1, Inv10, Inv11, Inv2, Inv3, Inv3.10, Inv3.3, Inv3.4, Inv3.5, Inv3.6, Inv3.7, Inv3.8, Inv3.9, Inv4, Inv5, Inv6, Inv7, Inv8, Inv9, IP-1, IPL, iRGD, iRGD-CDD, IRQ, IV, IX, JF06, JST-1, K8-lip, K9, KAFAK, KALA, Lyp-1, Lys9, M1, M2, M3, M4, M5, M511, M591, M593, M6, M630, M867, M918, M918(C-S), M918(R-K), m9R, MAP, Melittin, Met-Arg, MG2A, MG2d, Mgpe-10, Mgpe-3, Mgpe-4, Mgpe-9, MK2i, MMD45, MMD47, MMD49, MousePrp(1-28), MP, MPeptide14F-L, MPeptide8F-L, MPG, MPG-NLS, MPGMutant, MPGNLS, MPS, MPS-Galphai2, MPS-Galphai3, MTat2-Nat, MTpI-1, MTpI-2, MTpI-3, MTS, MTS-(5-FAM)-H3R8, Mutanttat-NBD, N-E5L-Sc18, n-NTD, N-pep5-cpp, N-terminusofX-Pep, N2-pep5-cpp, N3-pep5-cpp, NAP, NF-kB, NF1, NFL-TBS.40-63, NGR, nrdfTAT, NTD, NucleoplasminX, NYAD-36, NYAD-41, NYAD-66, NYAD-67, P(alpha), P(beta), P1, P16, P2, p21-ELP1-Bac, P22N, p28, P3, P4, P42-TAT, P5, p53-R11, p53-R3, p53-R7, P6, P7, P7-4, P7-5, P7-6, P7-7, P8, P9R, PA1, PA2, PA3, PA4, PA5, PA8, PACAP, PAF26, PAF95, PAF96, pAntp, pAntp(43-48), pAntp(43-50), pAntp(43-51), pAntp(43-52), pAntp(43-53), pAntp(43-54), pAntp(43-55), pAntp(43-56), pAntp(43-57), pAntp(43-58), pAntp(44-58), pAntp(45-58), pAntp(46-58), pAntp(47-58), pAntp(48-58), pAntp(49-58), pAntp(50-58), pAntp(51-58), pAntp(52-58), pAntp(53-58), pAntpHD, pAntpHD(3Pro), pAntpHD(43-58), pAntpHD(58-43), pAntpHD(Pro50), pAntpHD40P2, pAntpHD50A, pAntpmutant, PasR8-p27kip1C, PasR8-PAD, PC-CC9/miRNA, PD1, PD2, PDX-1-PTD, PE1, PE2, Pen, Pen-C-Cy5, Pen-Cys, Pen2W2F, PenArg, PenArg-Cys, PenetraMax, Penetratin, PEP-1, PEP-2, Pep-3, Pep1, Pep2, Pep3, Pep3(Mutant), pep-cpp, pepM, pepR, Peptide1, Peptide1-C3G, Peptide10, Peptide11, Peptide12, Peptide13, Peptide14, Peptide15, Peptide16, Peptide17, Peptide18, Peptide19, Peptide1C-GNS, Peptide1N-GNS, Peptide2, Peptide20, Peptide21, Peptide22, Peptide23, Peptide24, Peptide25, Peptide26, Peptide27, Peptide28, Peptide29, Peptide2C-GNS, Peptide2N-GNS, Peptide3, Peptide30, Peptide31, Peptide32, Peptide33, Peptide34, Peptide35, Peptide36, Peptide37, Peptide38, Peptide39, Peptide4, Peptide40, Peptide41, Peptide42, Peptide43, Peptide44, Peptide45, Peptide46, Peptide47, Peptide48, Peptide49, Peptide5, Peptide50, Peptide51, Peptide52, Peptide53, Peptide54, Peptide55, Peptide56, Peptide57, Peptide58, Peptide59, Peptide6, Peptide60, Peptide61, Peptide62, Peptide63, Peptide64, Peptide65, Peptide66, Peptide7, Peptide8, Peptide9, PF20, PF21, PF22, PF28, PF3, Phe-Oct-6, PHI21N (12-29), pISL, PL, PNIPAM-FL-TATPeptide, POD, polyarginine, Polyguanidinecomparators1, PolyP1, PolyP2, PolyP3(SAP), PolyP4, PolyP5, PolyP6, PolyP7, PolyP8, PolyP9, PolyR, PolyR-C-Cy5, ppTG, ppTG1, ppTG20, PR9, PreS2(41-52), PreS23SMutant, ProdeletionmutantofTat(48-60), Protamine, pTat, PTX-C-TAT-LP, PTX-N-TAT-LP, PTX-TAT-LP, PV-S4(13), pVEC, pVECmutant, PVreverse-S4(13), q-NTD, R10, R11, R11-PKI, R12, R15, R16, R2, R4, R5, R5H3, R6, R6-Pen(W-L), R6H3, R6L3, R6W3, R7, R7-KLA, R7-SRC1(1222-1245), R7-SRC1LXXLL, R7H3, R7W, R8, R8-GALA-liposome, R8-GALA-liposome-IgG, R8-lip, R8-lipo, R8-liposome, R8-p27kip1C, R8-PAD, R8-RGD, R8H3, R9, R9-PCP, R9-TAT, R9H3, RA, RALA, RALApeptide, Rath-FITC, Res1, Res2, Res3, Res4, Res5, Res6, Res7, Retro-pVEC, Retro-Tat(57-49), Rev(34-50), RevARM, RF, RFFF9, RFFW9, RFWF9, RFWW9, RGD, RGI, RGO, Rho-biotinyl-TP10, RIPL, RIPLpeptide, RL-9, rLF, RLW, RR-S4(13), RSG1.2, RSG1.2truncated, RSV-A1, RSV-A10, RSV-A11, RSV-A12, RSV-A13, RSV-A2, RSV-A3, RSV-A4, RSV-A5, RSV-A6, RSV-A7, RSV-A8, RSV-A9, RSV-B1, RSV-B2, RSV-B3, RTAT-ELPBC, rV1aR(102-113a), RV24, RVG-9LR, RW-9, RW16, RW9, RWFF9, RWFW9, RWMIX, RWR, RWWF9, S-TAT, S4(13), S4(13)-PV, S41, S6KR, S6R, S9R, S9RH, Sc18, SFTI-1, SFTI-M1, SFTI-M2, SFTI-M3, SFTI-M4, SFTI-M5, SG3, sgRNA-CPP, SKP, SN50, SR9, SRAMC105Y, ST1-104, ST2-104, ST9-104, Stearyl-NAP, Stearyl-NS, STR-H12R8, STR-H16R8, STR-H20R8, STR-H8R15, STR-H8R8, STR-R8, SV40, SweetArrowProtein(SAP)(E), SynB1, Synb1-ELP, SynB1-ELP-H1, Synb1-ELP-PKI, Synb1-ELP-TRTK, SynB3, SynB5, T7-LP, T7/TAT-LP-PTX, TAM-MP, TAM-rMP, TAMARA-peptide1, TAMARA-peptide2, TAMRA-IP-1, TAT, TAT-BID, Tat-C-Cy5, Tat-CG, Tat-Cys, TAT-cysteinepeptide, TAT-ELPBC, TAT-HA2, TAT-LP-PTX, TAT-NBD, TAT-PCP, Tat-PKI, Tat.48-60, Tat(37-53), Tat(37-60), Tat(43-60), TAT(47-57), Tat(48-57), Tat(48-59), Tat(48-60), Tat(49-55), Tat(49-56), Tat(49-57), Tat(50-57), Tat(51-57), Tat(TG), Tat2-Nat, TatARM, TatLK15, TatP59W, TatsMTS(TMG), TP, TP-10, TP-biot1, TP10, TP10-biot1, TP10-SRC1(1222-1245), TP10-SRC1LXXLL, TP11, TP12, TP13, TP14, TP15, TP16, TP2, TP4, TP5, TP6, TP7, TP8, TP9, Tpl, Tyr-Oct-6, Cyc-(L, D)-R6, Cyc-(L, D)-R7, Cyc-(L, D)-R8, Cyc-R3-R4, Cyc-R4, Cyc-R4-R3, Cyc-R5-R2, Cyc-R6, Cyc-R6-R1, Cyc-R7, Cyc-R8, Cyc-R9, D-Penetratin, D-R5, D-R6, D-R7, D-R8, d-R8-C6-NP, d-R8-INS-NP, D-R9, D-SFTI-1, D-SynB1, D-SynB3, D-Tat(49-57), D-Tat(57-49), dF4R8-p53C', DformofC105Y, DformofF3, DformofKLA, DformofpAntpHD(43-58), DformofpVEC, DformofSweatArrowProtein(SAP), Mitoparan(MitP), MMD68, Pepfect1, Pepfect14, Pepfect2, Pepfect3, Pepfect4, Pepfect5, Pepfect6, Peptide599, PeptideI, PeptideII, PeptideIII, PeptideIV, PeptideV, PF14, PF15, PF23, PF24, PF25, PF26, PF27, PF6, Pip6a, PN285, Polyguanidinecomparators2, probe1, probe2, probe3, pVECmutant, r12, r2(rR)3, R6, R7, R8, R8-RGD-lipo, R9, R9-GO-203, r9k, rR7, RVG-9DR, SFTI-M6, SFTI-M7, Stearyl-TP10, TAM-iMitP, TAM-iMP, TAM-MitP, TAM-riMitP, TAM-riMP, TAM-rMitP, Tat-DYQQD, Tat-ENAEYLR, Tat-NYQQN, Tat-OH, Tat-QNAQYLR, Tat (49-57), Tat(57-49), TP-biot13, TP10, TP102GD, TP102GL, TP104LD, TP104LL, TV-XIIa and Xentrypeptides, or any modified and/or synthetic peptides or peptide derivatives thereof. Chemical modifications of CPPs of particular utility are aliphatic and fatty acid modifications, such as covalent attachment of a lipid tail e.g. in the form of stearic acid, or any other type of lipid modification, such as the addition of a cholesterol moiety. Lipid modifications of particular relevance for complexation, internalization and overall efficacy in terms of EV loading include fatty acids comprising 10-30 carbon chosen from stearic acid, lauric acid, myristic acid, palmitic acid, arachidic acid, and behenic acid, or any derivatives thereof, especially un-saturated fatty acid derivative thereof. Chemical modifications of CPPs may further include one or more moieties covalently linked to the N-terminus of the peptide, the C-terminus of the peptide, or orthogonally anywhere along the peptide. These one or more moieties may be selected from a diverse range of chemical groups, such as acetyl groups, a stearyl groups, cholesteryl, a quinoline such as chloroquine or modified versions thereof, a poly-ethylene glycol, a nuclear localization signal, a nuclear export signal, an antibody or antibody fragment thereof, a peptide, a polysaccharide, a targeting molecule, cysteamide group, a cysteine, a thiol, an amide, a nitrilotriacetic acid, a carboxyl group, a linear or branched alkyl group, a primary or secondary amine, an osidic derivative, a lipid, a phospholipid, a fatty acid, a cholesterol, a polyethylene glycol, etc.

In yet another embodiment, the EVs as per the present invention may comprise at least one targeting moiety displayed on the surface of the EV, to even further enhance its therapeutic potential by targeting a tissue, an organ, or cell type of interest. The targeting moiety normally comprises a sequence of amino acids, which may be identified for instance through phage display or any other type of screening methodology. The targeting moiety is typically displayed on the EV surface through genetic engineering of the EV source cells, wherein the source cells are transfected to produce EVs comprising a fusion protein comprising the targeting moiety and an exosome protein. Alternative targeting approaches include attaching antibodies and/or antibody derivatives to the surface of EVs, to steer the vesicles to tissues, organs and/or cell types of interest.

In a further aspect, the present invention relates to a method of delivering a pharmacological agent to a target cell. Such delivery methods may comprise exposing a target cell, or a target tissue or target organ (which may include fluids and liquids such as blood, interstitial fluid, cerebrospinal fluid, etc.), to an EV as per the present invention. As above-mentioned, the EVs may comprise a targeting moiety expressed on its surface, or it may rely on natural tropism and targeting, or it may be non-targeted. Delivery to a target cell can be carried out in vitro and/or in vivo, depending on the context. Further, the present invention pertains to a method of altering the pharmacokinetic or pharmacodynamics profile of a pharmacological agent. This can be achieved through loading the pharmacological agent in question into an EV, which will naturally affect factors such as distribution, enzymatic activity, tissue penetration, etc.

In yet another aspect, the present invention pertains to pharmaceutical compositions comprising EVs comprising pharmacological agents conjugated to or complexed with CPPs. Typically, the pharmaceutical compositions as per the present invention comprise one type of therapeutic EV (i.e. a population of EVs comprising a certain desired pharmacological agent(s)) formulated with at least one pharmaceutically acceptable excipient, but more than one type of EV population may be comprised in a pharmaceutical composition, for instance in cases where a combinatorial treatment is desirable. The at least one pharmaceutically acceptable excipient may be selected from the group comprising any pharmaceutically acceptable material, composition or vehicle, for instance a solid or liquid filler, a diluent, an excipient, a carrier, a solvent or an encapsulating material, which may be involved in e.g. suspending, maintaining the activity of or carrying or transporting the EV population from one organ, or portion of the body, to another organ, or portion of the body (e.g. from the blood to any tissue and/or organ and/or body part of interest).

The present invention also relates to cosmetic and dermatological applications of pharmacological agent-carrying EVs. Thus, the present invention pertains to skin care products such as creams, lotions, gels, emulsions, ointments, pastes, powders, liniments, sunscreens, shampoos, etc., comprising a suitable EV, in order to improve and/or alleviate symptoms and problems such as dry skin, wrinkles, folds, ridges, and/or skin creases. In one embodiment, EVs (which comprise a pharmacological agent of interest) are obtained from a suitable EV-producing cell source with regenerative properties (for instance a mesenchymal stem cell) are comprised in a cosmetic cream, lotion, or gel for use in the cosmetic or therapeutic alleviation of wrinkles, lines, folds, ridges and/or skin creases.

In yet another aspect, the present invention relates to EVs as per the present invention for use in medicine. Naturally, when an EV comprising a pharmacological agent (conjugated and/or complexed with a CPP) in accordance with the present invention is used in medicine, it is in fact normally a population of EVs that is being used. The dose of EVs administered to a patient will depend on the amount pharmacological agent that has been loaded into the EV, the disease or the symptoms to be treated or alleviated, the administration route, the pharmacological action of the pharmacological agent itself, the inherent properties of the EV, as well as various other parameters of relevance.

The EVs and the EV populations as per the present invention may thus be used for prophylactic and/or therapeutic purposes, e.g. for use in the prophylaxis and/or treatment and/or alleviation of various diseases and disorders. A non-limiting sample of diseases wherein the EVs as per the present invention may be applied comprises Crohn's disease, ulcerative colitis, ankylosing spondylitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, non-alcoholic steatohepatitis (NASH), non-alcoholic fatty liver disease (NAFLD), fibrosis, Guillain-Barré syndrome, acute myocardial infarction, ARDS, sepsis, meningitis, encephalitis, liver failure, kidney failure, heart failure or any acute or chronic organ failure and the associated underlying etiology, graft-vs-host disease, Duchenne muscular dystrophy and other muscular dystrophies, lysosomal storage diseases such as Gaucher disease, Fabry's disease, MPS I, II (Hunter syndrome), and III, Niemann-Pick disease, Pompe disease, etc., neurodegenerative diseases including Alzheimer's disease, Parkinson's disease, Huntington's disease and other trinucleotide repeat-related diseases, dementia, ALS, cancer-induced cachexia, anorexia, diabetes mellitus type 2, and various cancers. Virtually all types of cancer are relevant disease targets for the present invention, for instance, Acute lymphoblastic leukemia (ALL), Acute myeloid leukemia, Adrenocortical carcinoma, AIDS-related cancers, AIDS-related lymphoma, Anal cancer, Appendix cancer, Astrocytoma, cerebellar or cerebral, Basal-cell carcinoma, Bile duct cancer, Bladder cancer, Bone tumor, Brainstem glioma, Brain cancer, Brain tumor (cerebellar astrocytoma, cerebral astrocytoma/malignant glioma, ependymoma, medulloblastoma, supratentorial primitive neuroectodermal tumors, visual pathway and hypothalamic glioma), Breast cancer, Bronchial adenomas/carcinoids, Burkitt's lymphoma, Carcinoid tumor (childhood, gastrointestinal), Carcinoma of unknown primary, Central nervous system lymphoma, Cerebellar astrocytoma/Malignant glioma, Cervical cancer, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Extracranial germ cell tumor, Extragonadal Germ cell tumor, Extrahepatic bile duct cancer, Eye Cancer (Intraocular melanoma, Retinoblastoma), Gallbladder cancer, Gastric (Stomach) cancer, Gastrointestinal Carcinoid Tumor, Gastrointestinal stromal tumor (GIST), Germ cell tumor (extracranial, extragonadal, or ovarian), Gestational trophoblastic tumor, Glioma (glioma of the brain stem, Cerebral Astrocytoma, Visual Pathway and Hypothalamic glioma), Gastric carcinoid, Hairy cell leukemia, Head and neck cancer, Heart cancer, Hepatocellular (liver) cancer, Hodgkin lymphoma, Hypopharyngeal cancer, Intraocular Melanoma, Islet Cell Carcinoma (Endocrine Pancreas), Kaposi sarcoma, Kidney cancer (renal cell cancer), Laryngeal Cancer, Leukemias ((acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia)), Lip and Oral, Cavity Cancer, Liposarcoma, Liver Cancer (Primary), Lung Cancer (Non-Small Cell, Small Cell), Lymphomas, AIDS-related lymphoma, Burkitt lymphoma, cutaneous T-Cell lymphoma, Hodgkin lymphoma, Non-Hodgkin, Medulloblastoma, Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic/Myeloproliferative Diseases, Myelogenous Leukemia, Chronic Myeloid Leukemia (Acute, Chronic), Myeloma, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic islet cell cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Pleuropulmonary blastoma, Prostate cancer, Rectal cancer, Renal cell carcinoma (kidney cancer), Retinoblastoma, Rhabdomyosarcoma, Salivary gland cancer, Sarcoma (Ewing family of tumors sarcoma, Kaposi sarcoma, soft tissue sarcoma, uterine sarcoma), Sezary syndrome, Skin cancer (nonmelanoma, melanoma), Small intestine cancer, Squamous cell, Squamous neck cancer, Stomach cancer, Supratentorial primitive neuroectodermal tumor, Testicular cancer, Throat cancer, Thymoma and Thymic carcinoma, Thyroid cancer, Transitional cell cancer of the renal pelvis and ureter, Urethral cancer, Uterine cancer, Uterine sarcoma, Vaginal cancer, Vulvar cancer, Waldenström macroglobulinemia, and/or Wilm's tumor.

The pharmacological agent-EVs as per the present invention may be administered to a human or animal subject via various different administration routes, for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the characteristics of the pharmacological agent or the EV population as such.

The methods of loading pharmacological agents into EVs described herein are highly efficient and easily scalable, and allow for the rapid production of pharmacological agent-loaded EVs in quantities needed for therapeutic administration. In certain embodiments of the foregoing aspects, loading of the EVs with the pharmacological agent occurs in 30 minutes or less, e.g. 5 minutes or less. In some embodiments, loading of the EVs occurs in 30 minutes, 20 minutes, 15 minutes, 10 minutes, 5 minutes, or 1 minute. In certain embodiments, at least 80% of the EVs incubated with a pharmacological agent CPP conjugate or CPP complex are loaded with the pharmacological agent. In a preferred embodiment, at least 90% of the EVs incubated with a pharmacological agent CPP complex/conjugate are loaded with the pharmacological agent. In exemplary embodiments, at least 91%, at least 92%, at least 93%, at least 94%, at least 95%, at least 96%, at least 97%, at least 98% or more of the EVs incubated with the pharmacological agent conjugates/complexes are loaded with the pharmacological agent. In one embodiment at least 99% of the EVs incubated with the pharmacological agent-CPP complex/conjugate are loaded with the pharmacological agent.

The methods of the present invention may also comprise exposing the EV source cells to serum starvation, hypoxia, bafilomycin, EV uptake inhibitors, exocytosis inducers or cytokines such as TNF-alpha and/or IFN-gamma, in order to influence the yield or properties of the resulting EVs into which pharmacological agents are subsequently loaded. The EV production scale and timeline will be heavily dependent on the EV-producing cell or cell line and may thus be adapted accordingly by a person skilled in the art.

The methods for loading pharmacological agents into EVs may further comprise a purification step, wherein the EVs are purified through a procedure selected from the group of techniques comprising liquid chromatography (LC), high-performance liquid chromatography (HPLC), spin filtration, tangential flow filtration, hollow fiber filtration, centrifugation, immunoprecipitation, flow field fractionation, dialysis, microfluidic-based separation, etc., or any combination thereof. In an advantageous embodiment, the purification of the EVs is carried out using a sequential combination of filtration (preferably ultrafiltration (UF), tangential flow filtration or hollow fiber filtration) and size exclusion liquid chromatography (LC). This combination of purification steps results in optimized purification, which in turn leads to superior therapeutic activity. Further, as compared to ultracentrifugation (UC), which is routinely employed for purifying EVs such as exosomes, sequential filtration-chromatography is considerably faster and possible to scale to higher manufacturing volumes, which is a significant drawback of the current UC methodology that dominates the prior art. Another advantageous purification methodology is tangential flow filtration (TFF), which offers scalability and purity, and may be combined with others types of purification techniques such as filtration. Purification techniques are typically deployed prior to loading exposing the EVs to the pharmacological agent-CPP conjugates and/or complex, in order to avoid interference from e.g. serum proteins, or unspecific loading into EVs having undesirable characteristics or features. A typical workflow for the production of pharmacological agent-carrying EVs is (1) creation of a stable cell line expressing EVs having a targeting moiety displayed on their surface, (2) in an optional step purification of large quantities of such genetically engineered EVs, (3) introduction of at least one pharmacological agent into the EVs in question, with the aid of at least one CPP. CPPs may be mixed with the pharmacological agent in a separate vessel and/or e.g. in a microfluidic device prior to exposure to EVs, for instance to enable complex formation prior to interaction with the EV population. Alternatively, complex formation or covalently conjugated CPP-pharmacological agents may be mixed directly with the EVs, typically in the form or purified EV populations.

It shall be understood that the above described exemplifying aspects, embodiments, alternatives, and variants can be modified without departing from the scope of the invention. The invention will now be further exemplified with the enclosed examples, which naturally also can be modified considerably without departing from the scope and the gist of the invention.

EXAMPLES

Example 1: Immune Cell-Derived EVS Loaded with CPP-Doxurubicin Conjugates

Peripheral blood mononuclear cells (PBMCs) were extracted from whole blood of wildtype mice and cultured at an appropriate density in a 10 cm dish. The cell media was removed after 24 hours and the cells were washed with PBS 3 times. New fresh EV-depleted media or serum free media was added to the cells and were incubated for 48 hours. The serum containing cell culture media that the cells are grown in is normally depleted of foreign EVs and microparticles by ultracentrifugation at 110 000 g overnight before incubation with the cells. Alternatively, serum free media is applied in its place, such as OptiMEM or DMEM.

Conditioned media from the PBMC culture was purified using battery of techniques, in this case ultrafiltration or tangential flow filtration (TFF) with sequential LC.

The CPP penetratin was covalently conjugated to the cardiotoxic anticancer agent doxorubicin as previously described by Shi et al., Int J Nanomedicine, 2012; 7:1613-21.

A composition comprising a suitable concentration (for instance, $10^{12}$ (i.e. 10 trillion) particles/ml) of PBMC EVs obtained from the TFF or UF/LC purification steps were mixed with a buffer containing penetratin-doxorubicin conjugates at a concentration of 1 mM. After a 30-minute incubation, non-loaded penetratin-doxorubicin conjugates were removed from the loaded EVs using ultrafiltration with 10 kDa cutoff.

The cytotoxicity of free doxorubicin, EVs loaded with penetratin-doxorubicin conjugates, and free penetrating-doxorubicin conjugates were determined using the MTT assay. MDA-MB-231 or MCF7 cells ($1\times10^5$ cells/100 μl/well) were cultured in 96-well plates at 37° C. and 5% $CO_2$. Aqueous drug solutions as per above were dissolved in culture medium at final concentrations of 1, 5, 10, 15 and 20 μM. After an incubation time of 24 h, the MTT solution (2 mg/ml in PBS) was added to the plate and were incubated for 24 h, and the cells were lysed with 50% N,N-dimethyl-formamide containing 20% SDS, pH 4.5. The absorbance at 570 nm was measured for each well by the SpectraMax M5 instrument (Molecular Devices, CA). The absorbance of control cells was taken as 100% viability, and the values of the treated cells were calculated as a percentage of control. The results are shown in FIG. 1, indicating that EVs loaded with penetratin-doxorubicin conjugates display similar anticancer effects as free CPP-doxorubicin conjugates, warranting further in vivo investigation.

Figure 2:
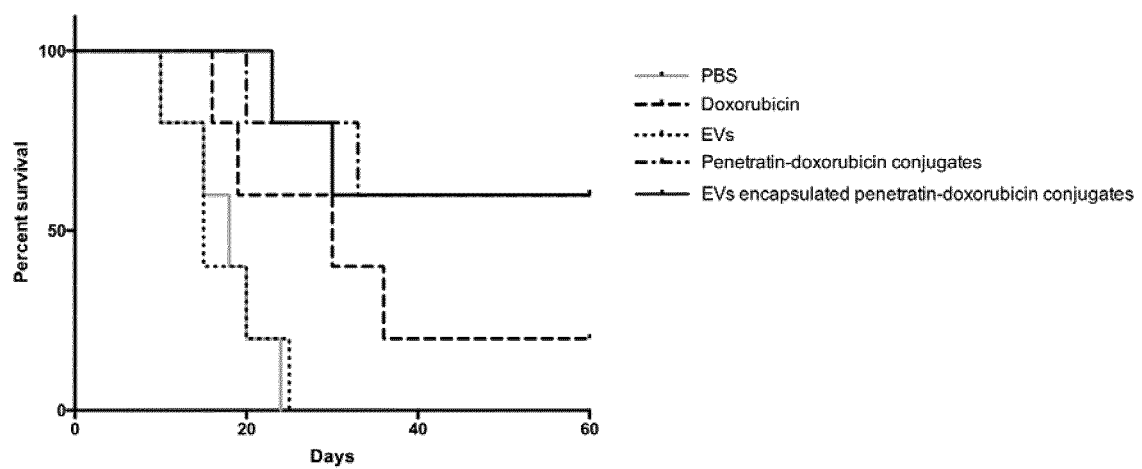
FIG. 2 shows the antitumor effect in vivo of immune cell-derived EVs loaded with CPP-doxurubicin conjugates: L1210 syngeneic leukemia-bearing mice were treated with free doxorubicin, EVs loaded with penetratin-doxorubicin conjugates, or free penetrating-doxorubicin conjugates, and Kaplan-Meier curve was used to analyze survival.

Example 2: In Vivo Evaluation of Penetratin-Doxorubicin Conjugates Loaded into Immune Cell EVs The penetratin-doxorubicin EVs in Example 1 were tested in an in vivo tumor model, using female DBA/2 mice (weighing 16-20 g). On day zero, five groups of mice were inoculated via i.p. injection with L1210 tumour cells ($2.5\times10^6$) in 0.5 ml of RPMI1640. Treatment was initiated 1 day after injection of tumour cells and was administrated as a single i.v. dose via the lateral tail vein. The animals were treated with penetratin-doxorubicin conjugates, EVs comprising penetratin-doxorubicin conjugates, empty EVs, and free doxorubicin with a doxorubicin dose of 5 mg/kg. Survival time was recorded in days after tumour injection. The mean and median survival time and the statistical significance of the results were determined employing a two-tailed Wilcoxon's ranking test. All data obtained for repeated experiments were pooled and utilised for statistical analysis. Results are shown in FIG. 2, indicating that EVs loaded with penetratin-doxorubicin conjugates exhibit similar efficacy as free penetratin-doxorubicin conjugates. However, the cardiotoxicity of doxorubicin was reduced considerably upon EV-mediated delivery (data not shown).

Figure 3:
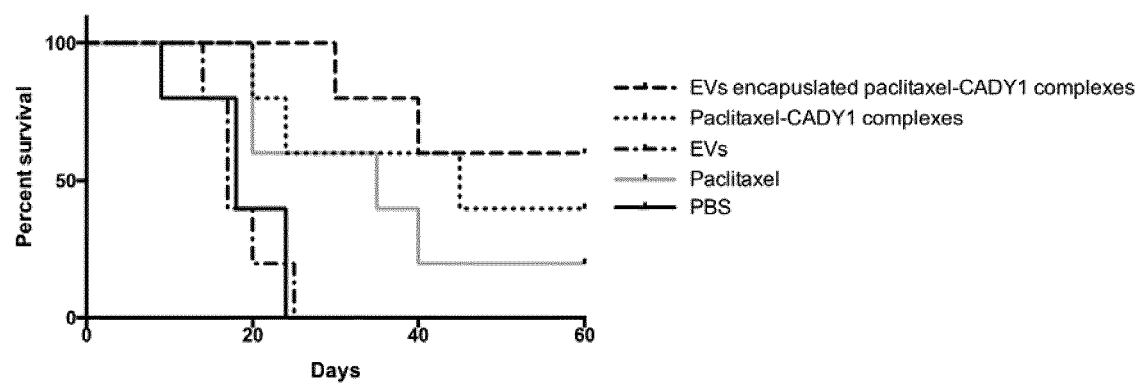
FIG. 3 shows the antitumor effect in vivo of DC-EVs loaded with CADY1-paclitaxel complexes: L1210 syngeneic leukemia-bearing mice were treated with EVs comprising paclitaxel-CADY1 complexes, paclitaxel-CADY1 complexes alone, empty EVs or free paclitaxel with a paclitaxel dose of 10 mg/kg and Kaplan-Meier curve was used to analyze survival.

Example 3: In Vivo Evaluation of DC-EVs Loaded with CADY1-Paclitaxel Complexes EVs were obtained as stated in Example 1 but from dendritic cells (DCs) as a cell source. Paclitaxel and the amphipathic CPP CADY-1 (GLWWKAWWKAWWKSLWWRKRKRKA) (SEQ ID NO: 1) were mixed at various molar ratios and incubated at 22° C. for 1 hour. Varying amounts of CADY-1 were used (100 μg, 500 μg, 2.5 mg, 5 mg and 10 mg), whilst the amount of paclitaxel remained at 100 μg. The final weight ratios of paclitaxel to CADY-1 were 1:1, 1:5, 1:25, 1:50 and 1:100 respectively. The same mouse model as stated in Example 2 was utilized, but instead EVs which had been incubated with paclitaxel-CADY1 complexes were used, after the free paclitaxel-CADY1 complexes had been removed through ultrafiltration. EVs comprising paclitaxel-CADY1 complexes, paclitaxel-CADY1 complexes alone, empty EVs and free paclitaxel with a paclitaxel dose of 10 mg/kg were tested in vivo in the tumor model as described above. In analogy with the results seen with the penetratin-doxorubicin EVs, EVs comprising paclitaxel-CADY1 complexes exhibited strong antitumor effects (FIG. 3).

Example 4: In Vivo Evaluation of MSC-EVs Loaded with Stearylated TP10-Azathioprine Complexes for the Treatment of Colitis EVs were purified as stated in example 1 from cell culture medium obtained from mesenchymal stromal cells of bone marrow and Wharton's jelly origin. Varying amounts of stearyl-TP10 was used (100 μg, 500 μg, 2.5 mg, 5 mg and 10 mg), whilst the amount of azathioprine remained at 100 μg. The final weight ratios of azathioprine to stearyl-TP10 were 1:1, 1:5, 1:25, 1:50 and 1:100 respectively and incubated at 22° C. for 10 minutes, 30 minutes, 2 hours, and 6 hours. Varying amounts of the CPP were used, whilst the concentration of azathioprine remained constant. The complexes obtained at the optimal molar ratio of CPP to pharmacological agent were subsequently mixed with purified populations of MSC-EVs and allowed to incubate at 37° C. for 10 minutes, 30 minutes, 2 hours, and 6 hours. Maximum loading of EVs was obtained within 30 minutes and the free azathioprine was removed by ultrafiltration. Then Azathioprine-loaded MSC-EVs were thus subsequently administered to mice with TNBS-induced colitis.

TNBS-induced colitis. which mimics Crohn's, disease results in a cytokine storm, diarrhoea, decrease in weight, and inflammation in gut. 24 mice were divided into four treatment groups, with 6 mice per group. The mice were pre-sensitized by applying 150 µl of olive oil-acetate solution with 2% TNBS, on the skin, 1 week prior to colitis induction. Colitis was then induced by giving a rectal infusion of 100 µl solution containing 1.5% TNBS in 40% ethanol. Immediately post colitis induction, single dose of 30 µg azathioprine-containing EVs in 120 µl.

Figure 4:
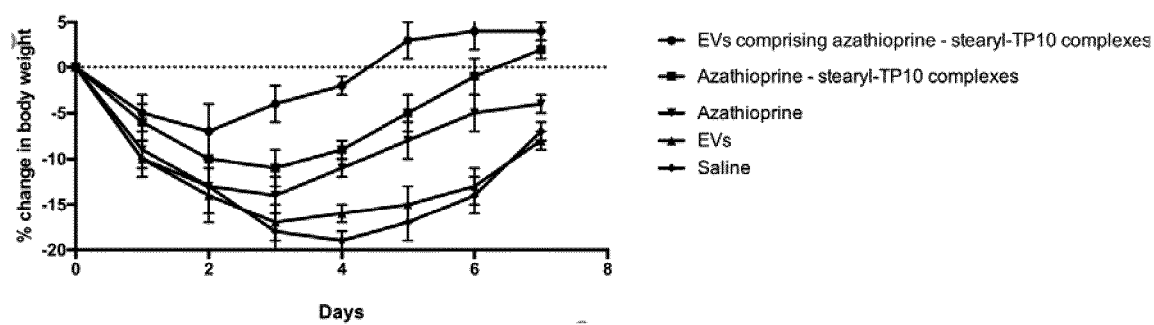
FIG. 4 shows the anti-inflammatory effect of MSC-EVs loaded with stearylated TP10-azathioprine complexes in TNBS induced colitis mice. EVs comprising azathioprine-stearyl-TP10 complexes, azathioprine-stearyl-TP10 complexes alone, empty EVs or free azathioprine with an azathioprine dose of 1.5 mg/kg were administrated intravenously through the tail vein and the bodyweight was recorded daily for next 7 days. Data plotted as percentage of basal body weight.

EVs comprising azathioprine-stearyl-TP10 complexes, azathioprine-stearyl-TP10 complexes alone, empty EVs and free azathioprine with a azathioprine dose of 1.5 mg/kg were administrated intravenously through the tail vein and the bodyweight was recorded daily for next 7 days. Mice treated with azathioprine-TP10 EVs displayed the quickest recovery after colitis reduction, as shown in FIG. 4.

Figure 5:
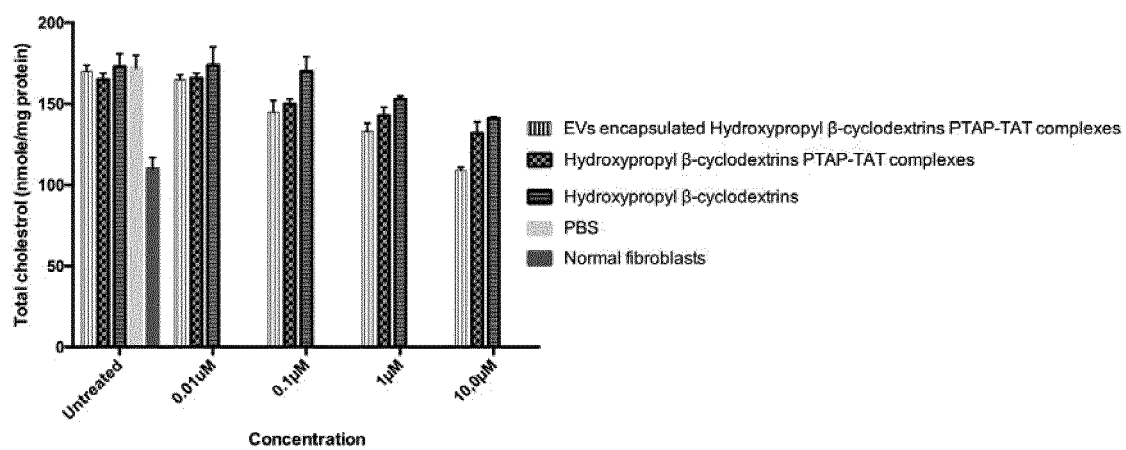
FIG. 5 shows the cholesterol-reducing effect of EVs encapsulated with hydroxypropyl β-cyclodextrins PTAP-TAT complexes in NPC disease patient-derived skin fibroblasts: The amount of total cholesterol in normal and NPC1 fibroblasts treated with EVs encapsulated with hydroxypropyl β-cyclodextrins PTAP-TAT complexes, hydroxypropyl β-cyclodextrins PTAP-TAT complexes and free hydroxypropyl β-cyclodextrins. Cells were treated with different doses (0.01, 0.1, 1 and 10 μM) and after 24 hours, filipin staining was used to determine the amount of total cholesterol.

Example 5: In Vitro Evaluation of Adipocytes-EVs Loaded with Hydroxypropyl/β-cyclodextrins PTAP-TAT complexes Immortalized adipocyte cells were plated in 15 cm dish. The cells were then transfected with hydroxypropyl β-cyclodextrins PTAP-TAT complexes. Varying amounts of PTAP-TAT was used (100 µg, 500 µg, 2.5 mg, 5 mg and 10 mg), whilst the amount of hydroxypropyl 3-cyclodextrins remained constant at 100 µg. The final weight ratios of of hydroxypropyl β-cyclodextrins to PTAP-TAT were 1:1, 1:5, 1:25, 1:50 and 1:100 respectively and incubated at 22° C. for 60 minutes. The cell media was removed after 4 hours and the cells were washed with PBS 3 times. New fresh EV-depleted media or serum free media was added to the cells and were incubated for 48 hours. EVs were then purified from conditioned medium as mentioned in example 1. Cholesterol reducing effect of EVs encapsulated with hydroxypropyl β-cyclodextrins PTAP-TAT complexes, hydroxypropyl β-cyclodextrins PTAP-TAT complexes and free hydroxypropyl β-cyclodextrins was evaluated on Nieman-Pick type C disease patient derived skin fibroblasts using Filipin staining, by staining the cells with Filipin III stain for 45 minutes at room temperature, 24 hours after EV treatment. The results are shown in FIG. 5, indicating that EVs loaded with hydroxypropyl β-cyclodextrins PTAP-TAT complexes display potent cholesterol reduction effect as compare to free drug.

Figure 6:
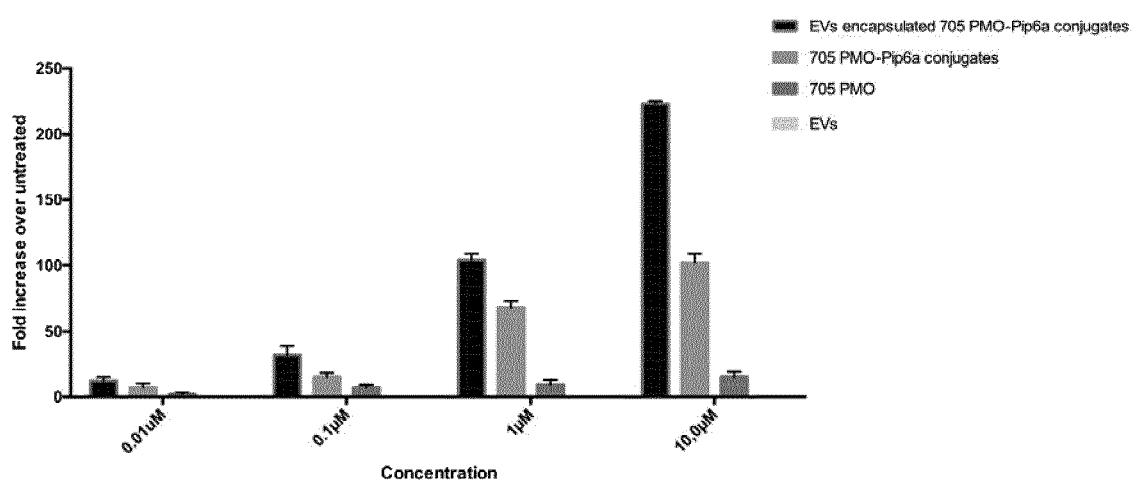
FIG. 6 shows splice correction after treatment with EV-encapsulated Pip6a-PMO conjugates: Splice correction in Huh7 pLuc 705 cells over untreated cells upon treatment with EVs comprising 705-Pip6a conjugates, 705-Pip6a conjugates alone, empty EVs and free 705 SSO at different concentrations (0.01, 0.1, 1 and 10 μM) after 24 hours. Graph showing relative luminescence values normalized to untreated cells.
Figure 7:
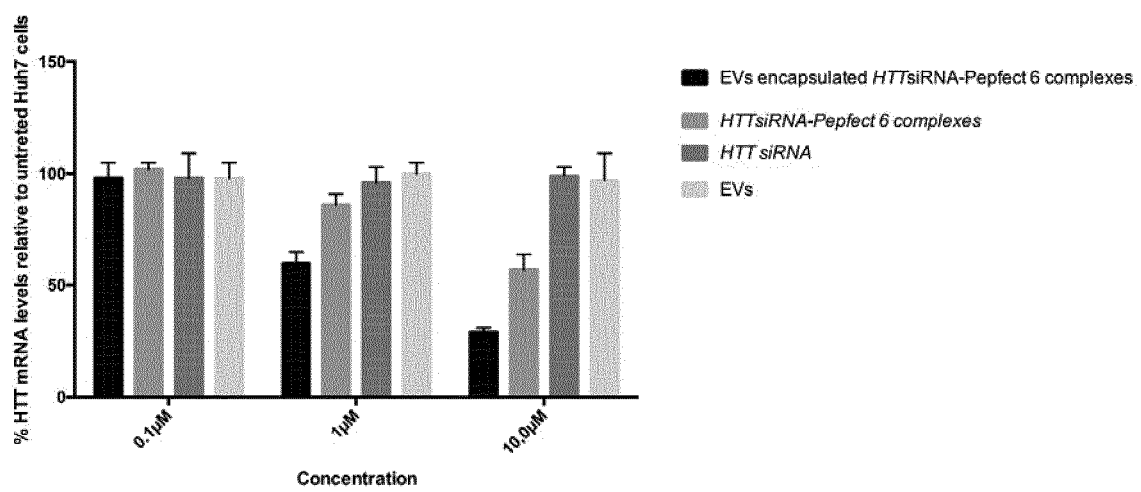
FIG. 7 shows gene knockdown after treatment with EV encapsulated HTT siRNA-Pepfect 6 complexes: mRNA levels of Huntington gene in Huh7 cells over untreated cells upon treatment with EVs comprising HTT siRNA-Pepfect 6 complexes, HTT siRNA-Pepfect 6 complexes alone, empty EVs and free HTT siRNA at different concentrations (0.1, 1, and 10 μM) after 24 hours. Graph showing Huntington mRNA levels normalized to untreated cells.

Example 6: In Vitro Evaluation of MSC-EVs Loaded with 705 PMO Splice Switching Oligonucleotide-Pip6a Conjugates EVs were obtained from MSC EVs as stated in Example 1. Splice switching oligonucleotide(SSO) 705 with phosphorodiamidate morpholino oligomer(PMO) modification was conjugated with CPP Pip6a as described in Betts C. et. al, Mol. Ther. Nucleic Acids. 2012. EVs were incubated with CPP conjugates as stated in Example 1, free conjugates were remove through ultrafiltration. EVs comprising 705-Pip6a conjugates, 705-Pip6a conjugates alone, empty EVs and free 705 SSO were tested in vitro in the Huh7 705 reporter cell line, after 24 hours, cells were lysed using 0.1% tritonX-100 in PBS, luminescence values were then determined using Promega firefly luciferase kit. The results are shown in FIG. 6, indicating potent splice switching activity with EVs loaded with SSO-CPP complexes over SSO-CPP complexes alone.

Example 7: In Vitro Evaluation of Fibroblast EVs Loaded with siRNA-Pepfect 6 Complexes EVs were obtained as described in Example 1 but instead from foreskin derived fibroblast. siRNA targeting Huntington gene was complexed with CPP Pepfect 6 at various molar ratio and incubated at 22° C. for 1 hour. Varying amounts of Pepfect 6 were used (100 µg, 500 µg, 2.5 mg, 5 mg and 10 mg), whilst the amount of siRNA remained at 100 µg. The final weight ratios of siRNA to Pepfect 6 were 1:1, 1:5, 1:25, 1:50 and 1:100 respectively. EVs were incubated with CPP complexes as stated in Example 1, free complexes were remove through ultrafiltration. EVs comprising siRNA CPP complexes, siRNA-Pepfect 6 complexes alone, empty EVs and free siRNA were tested in vitro for Huntington gene silencing in Huh7 cell line, after 24 hours cells were harvested and RNA was isolated using Trizol purification method. cDNA was then reverse transcribed form the RNA using High capacity cDNA reverse transcription kit, cDNA was then used to run quantitative PCR for determining Huntington mRNA levels. Consistent with the results observed in Example 6, EVs loaded with siRNA-CPP complexes showed potent gene silencing over siRNA-CPP complexes alone.

---

The invention claimed is:

1. A method for loading exosomes with at least one pharmacological agent, comprising exposing a population of exosomes to at least one pharmacological agent and at least one cell-penetrating peptide (CPP), wherein the at least one pharmacological agent and the at least one CPP are present in the form of a non-covalent complex.

2. The method according to claim 1, further comprising an electroporation step or the use of a lipid-based transfection reagent.

3. A method for loading an exosome with at least one pharmacological agent, comprising the steps of:
   i. exposing a population of exosome source cells to the at least one pharmacological agent and at least one cell-penetrating peptide (CPP), wherein the at least one pharmacological agent and the at least one CPP are present in the form of a non-covalent complex; and,
   ii. harvesting exosomes produced by the exosome source cells, wherein the exosomes comprise said pharmacological agent.

4. The method according to claim 3, further comprising combining step (i) with electroporation of the exosome source cells.

5. The method according to claim 1, wherein the non-covalent complex between the at least one CCP and the at least one pharmacological agent are present in the form of nanoparticles with positive or negative zeta potential.

6. The method according to claim 3, wherein the non-covalent complex between the at least one CCP and the at least one pharmacological agent are present in the form of nanoparticles with positive or negative zeta potential.

* * * * *